United States Patent [19]

Kondo et al.

[11] Patent Number: 4,543,350

[45] Date of Patent: Sep. 24, 1985

[54] CARCINOSTATIC AGENT

[75] Inventors: Tatsuhei Kondo, Nagoya; Noboru Takabe, Toyohashi; Takeshi Horiba, Aichi, all of Japan

[73] Assignee: Sanyo Machine Works, Ltd., Aichi, Japan

[21] Appl. No.: 515,602

[22] Filed: Jul. 21, 1983

[30] Foreign Application Priority Data

Nov. 9, 1982 [JP] Japan ................................. 57-196304

[51] Int. Cl.$^4$ ..................... C07C 103/52; A61K 37/00; C12P 21/00; C12P 21/02; C12R 1/89
[52] U.S. Cl. .......................................... 514/18; 514/2; 435/68; 435/70; 435/946; 260/112.5 R; 424/177
[58] Field of Search ...................... 260/112.5; 424/195, 424/177; 435/946, 69, 70, 68

[56] References Cited

PUBLICATIONS

Whitaker et al, *Chem. Abstr.*, vol. 80, 1974, No. 78377z, "Pharmacological Evaluation of an Extract from *Eisenia bicyclis*".
Usui, Taichi et al, *Chemical Abstracts*, vol. 93, 216014a, "Isolation of Highly Purified Fucoidan from *E. bicyclis* and Its Anticoagulant and Anti-Tumor Activities", 1980.
Whitaker et al., *Proc. of Food and Drugs, from the Sea*, 3d, pp. 97–103 (1972).
*Bulletin of the Agricultural Chemical Society of Japan*, vol. 15, pp. 370–376 (1939) (in Japanese, with English translation).
*Abstracts from the Bulletin of the Agricultural Chemical Society of Japan*, vol. 15, pp. 78–79 (1939) (in English).
*Journal of Organic Chemistry*, vol. 39, pp. 180–182 (1974).
*Agricultural and Biological Chemistry*, vol. 30, pp. 495–499 (1966).
*Agricultural and Biological Chemistry*, vol. 44, pp. 1965–1966 (1980).

*Primary Examiner*—Thomas G. Wiseman
*Assistant Examiner*—Robin Teskin
*Attorney, Agent, or Firm*—Lyon & Lyon

[57] ABSTRACT

A carcinostatic agent having an immunopotentiating carcinostatic effect which contains as an active ingredient Eisenin (tripeptide) of the general formula:

L-Pyroglu-L-Glu-L-Ala wherein Pyroglu, Glu and Ala represent pyroglutamic acid, glutamic acid and alanine respectively.

7 Claims, 5 Drawing Figures

CARCINOSTATIC AGENT

BACKGROUND OF THE INVENTION

This invention relates to a carcinostatic agent having an immunopotentiating carcinostatic effect which contains as an active ingredient Eisenin which is a tripeptide obtained by extraction from seaweed *Eisenia bicyclis* or by synthesis, and more specifically, it relates to a carcinostatic agent having an immunopotentiating carcinostatic effect which contains as an active ingredient Eisenin (tripeptide) of the general formula:

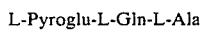

wherein Pyroglu, Gln and Ala represent pyroglutamic acid, glutamine and alanine, respectively.

SUMMARY OF THE INVENTION

An object of this invention is to provide a carcinostatic agent having an immunopotentiating carcinostatic effect which contains as an active ingredient Eisenin (tripeptide) of the general formula:

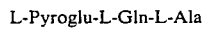

wherein Pyroglu, Gln and Ala represent pyroglutamic acid, glutamine and alanine, respectively.

Eisenin is a tripeptide extracted from seaweed *Eisenia bicyclis,* and it has lately become possible to synthesize it. It is colorless long needles having a silk-thread gloss, positive in Biuret reaction, shows somewhat shrinkage at a melting point of 180° C. and decomposes on melting at 225°–226° C., and its aqueous solution is acidic. This invention has been accomplished based on a new development of Eisenin as a carcinostatic agent having an immunopotentiating carcinostatic effect.

In particular, the anti-tumor effect of Eisenin in accordance with this invention is not a direct effect but its effect is manifested in such way that non-specific immunological ability of the vital body is increased, and since Eisenin itself has a simple tripeptide structure, its production etc. is easy. Further, since Eisenin is crystalline, it may be formed into fine powder, and since it is water soluble, it may be processed into various pharmaceutical forms such as injections, tablets, ointments and suppositories using pharmaceutically acceptable carriers and excipients commonly employed in the pharmaceutical practice.

DETAILED DESCRIPTION OF THE PREFERRED EMBODIMENTS

As the result of the present inventor's study on Eisenin obtained by extraction from seaweed *Eisenin bicyclis* or synthesis, it has now been found that this is effective as a carcinostatic agent having an immunopotentiating carcinostatic effect. The results of animal experiments etc. conducted on the immunopotentiating carcinostatic effect of Eisenin are described hereinbelow. In the figures and tables, the legends Eisenin Treated and Nontreated means Eisenin administered and not administered respectively.

(1) Animal Experiments

Figure 1:
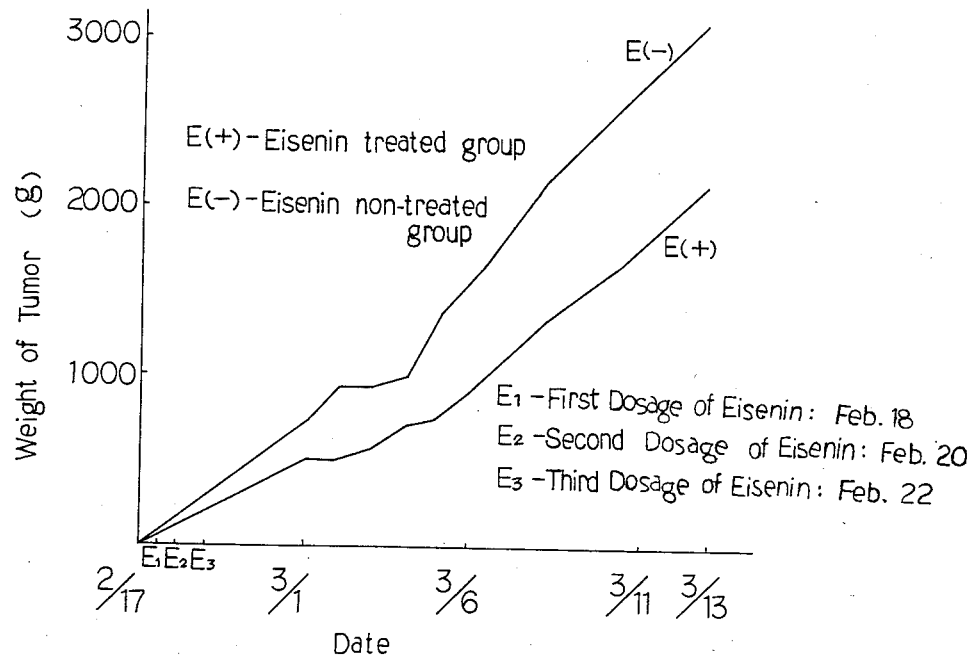
FIG. 1 is a graph showing the anti-tumor effect of Eisenin against the isologous allogenic tumor.
Figure 2:
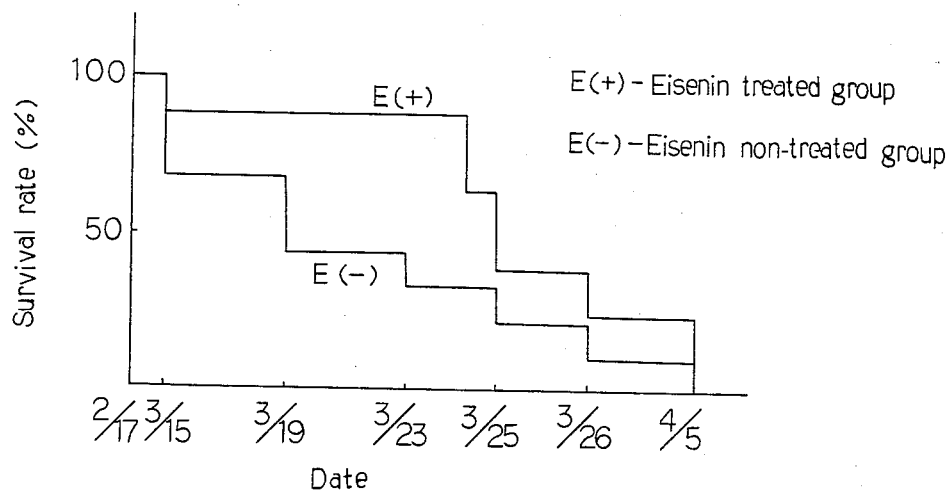
FIG. 2 is a graph showing the life prolonging effect of the same.

The animals used as experimental materials were Balb/C mice and nude mice, and the tumors used were Colon (Balb/C Colon cancer) and Sarcoma 180.

a. 1,000,000 Cells of Colon 26 were transplanted subcutaneously to Balb/C mice. Eisenin was intraperitoneally administered to the mice at a rate of 5 mg per animal every other day three times, and the weight of the tumor and the survival rate were examined. The results thereof are set forth in FIG. 1 and FIG. 2.

b. 1,000,000 Cells of Colon 26 were transplanted subcutaneously to nude mice, Eisenin was intraperitoneally administered to the mice at a rate of 5 mg per animal every other day twice, and the weight of the tumor and the survival rate were examined. The results are set forth in FIG. 3 and FIG. 4.

c. 1,000,000 Cells of Sarcoma 180 were transplanted subcutaneously to Balb/C mice, Eisenin was intraperitoneally and orally administered to the mice at a rate of 5 mg per animal every other day three times, and the weight of the tumor was examined. The results are set forth in FIG. 5.

d. $10^6$ Cells of sheep red blood cells (S R bc) were intravenously injected to Balb/C mice, four days later, $10^8$ cells of sheep red cells and phosphate buffer solution (PBS) were subcutaneously injected to the sole of the left foot and at the same time the phosphate buffer solution (PBS) alone was subcutaneously injected to the sole of the right foot, and two days later, the thickness of both feet were measured to examine the delayed hyper-sensitivity. The results are set forth in Table 1.

TABLE 1

| Delayed Hyper-sensitivity | | | | | | | |
|---|---|---|---|---|---|---|---|
| Group 1 T (+). E (+) | | | | Group 2 T (+). E (−) | | | |
| L | R | L − R | $\frac{L-R}{R} \times 100$ | L | R | L − R | $\frac{L-R}{R} \times 100$ |
| 1.59 | 1.57 | 0.02 | 1 | 1.91 | 1.69 | 0.22 | 13 |
| 1.56 | 1.54 | 0.02 | 1 | 1.83 | 1.83 | 0 | 0 |
| 1.87 | 1.68 | 0.19 | 11 | 1.91 | 1.80 | 0.11 | 6 |
| 1.95 | 1.49 | 0.46 | 31 | 1.86 | 1.67 | 0.19 | 11 |
| 1.75 | 1.67 | 0.08 | 5 | 1.78 | 1.69 | 0.09 | 5 |
| 1.54 | 1.57 | 0.03 | 0 | 1.96 | 1.72 | 0.24 | 14 |
| 1.58 | 1.54 | 0.04 | 3 | 1.71 | 1.52 | 0.19 | 13 |
| 1.90 | 1.65 | 0.25 | 15 | 1.82 | 1.69 | 0.13 | 8 |
| — | — | — | — | 1.83 | 1.87 | 0.04 | 0 |
| — | — | — | — | 1.77 | 1.77 | 0 | 0 |

TABLE 1-continued

| Delayed Hyper-sensitivity | | | |
|---|---|---|---|
| Average | 8 | Average | 7 |

| Group 3 T (−). E (−) | | | | Group 4 T (−). E (+) | | | |
|---|---|---|---|---|---|---|---|
| L | R | L − R | $\frac{L-R}{R} \times 100$ | L | R | L − R | $\frac{L-R}{R} \times 100$ |
| 1.90 | 1.85 | 0.05 | 3 | 2.09 | 1.86 | 0.23 | 12 |
| 1.95 | 1.85 | 0.10 | 5 | 2.18 | 1.98 | 0.20 | 10 |
| 2.08 | 1.92 | 0.16 | 8 | 1.84 | 1.86 | 0.02 | 0 |
| 1.89 | 1.78 | 0.11 | 6 | 1.93 | 1.81 | 0.12 | 7 |
| 1.91 | 1.82 | 0.09 | 5 | 1.87 | 1.72 | 0.15 | 9 |
| 2.01 | 1.78 | 0.23 | 13 | 1.93 | 1.61 | 0.32 | 20 |
| 1.97 | 1.91 | 0.06 | 3 | 1.87 | 1.88 | 0.01 | 0 |
| 1.99 | 1.80 | 0.19 | 11 | 1.93 | 1.87 | 0.06 | 3 |
| 1.92 | 1.82 | 0.10 | 5 | — | — | — | — |
| 1.92 | 1.75 | 0.17 | 10 | — | — | — | — |
| Average | | | 7 | Average | | | 8 |

Notes:
1. T (+) means tumor transplanted; T (−) means tumor not transplanted.
2. E (+) means Eisenin treated; E (−) means Eisenin non-treated.
3. L means the thickness of the left foot (mm);
   R means the thickness of the right foot (mm).

(2) In Vitro Assay a. Sensitivity Test

Colon 26 was tissue cultured, and brought into contact with Eisenin at various concentrations for 3 days, tritium thymidine, uridine and leucine were added respectively, and the inclusion into the cells was examined to determine the inhibition index. The results of the examination on the influence of Eisenin on the syntheses of DNA, RNA and protein are set forth in Table 2.

TABLE 2

| | Sensitivity Test | | | | | |
|---|---|---|---|---|---|---|
| Concentration of Eisenin (mg/ml) | 1.0 | 0.1 | 0.01 | 0.001 | 0.0001 | Control |
| Counts per Minute in the Case of Tritium Thymidine (CPM) | 140430 | 190120 | 207474 | 220010 | 231236 | 218622 |
| | 171170 | 203872 | 229569 | 213816 | 219336 | 220775 |
| | 163554 | 201151 | 240628 | 221170 | 224786 | 245962 |
| | 176167 | 223845 | 246273 | 213017 | 233612 | 226495 |
| Average | 170297 | 198381 | 238823 | 218332 | 229878 | 221964 |
| I.I. (%) | 23 | 11 | 8 | 2 | 0 | |
| Counts per Minute in the Case of Uridine (CPM) | 27088 | 32774 | 37043 | 39415 | 32836 | 32553 |
| | 20903 | 25271 | 33211 | 31675 | 29585 | 31801 |
| | 19954 | 24222 | 31498 | 28671 | 24135 | 30304 |
| | 22463 | 26786 | 34408 | 33161 | 29958 | 27653 |
| Average | 21107 | 25426 | 33039 | 31169 | 30793 | 31553 |
| I.I. (%) | 33 | 19 | 0 | 0 | 2 | |
| Counts per Minute in the Case of Leucine (CPM) | 6826 | 13311 | 12285 | 13620 | 12952 | 14674 |
| | 6150 | 12566 | 11020 | 14230 | 11936 | 11382 |
| | — | 8076 | 12097 | 13379 | 11808 | 12690 |
| | 6587 | 7076 | 11318 | 11355 | 10952 | 14350 |
| Average | 6521 | 11318 | 11478 | 13743 | 12232 | 13905 |
| I.I. (%) | 53 | 19 | 17 | 1 | 12 | |

Notes:
(1) Inhibition Index (I.I.) is calculated from the following equation, and where I.I. exceeds 75%, it is judged effective.

$$I.I. = \frac{CPM\ (Control) - CPM\ (Drug)}{CPM\ (Control)} \times 100$$

(2) Measurement is made on a scintillation counter.

b. Cytotoxicity Test

Balb/C mice were intraperitoneally administered with 15 mg of Eisenin, and the control group was administered with starch. Further, the target cell employed was BW 5174 (thymoma of AKR mouse). The spleen cells and the intraperitoneal cells were respectively divided into the adherent cells and the non-adherent cells, and cytotoxicity was examined in each case. The results are set forth in Table 3.

TABLE 3

| Cytotoxicity Test | | |
|---|---|---|
| | Eisenin Administered | Control Group |
| Spleen Cells | | |
| Total | 24% | 23% |
| Non-adherent Cells (Natural Killer) | 13% | 15% |
| Adherent Cells (Macrophage) | 10% | 10% |
| Intraperitoneal Cells | | |
| Total | 24% | −8% |
| Non-adherent Cells (Natural Killer) | 32% | 2% |
| Adherent Cells (Macrophage) | 17% | −5% |

Notes:
(1) Percent Cytotoxicity (%) in Table 3 is based on the following equation:

$$\text{Percent Cytotoxicity} = \frac{\text{Test Count} - \text{Minimum Count}}{\text{Maximum Count} - \text{Minimum Count}} \times 100$$

(2) Measurement is made by $^{51}Cr$ release assay.

(3) Acute Toxicity Test

The results obtained when 9 Balb/C mice (average body weight 20 g) were intraperitoneally administered with Eisenin are set forth in Table 4.

TABLE 4

| Acute Toxicity Test | | |
|---|---|---|
| | | No. of Death |
| Dosage of Eisenin (g/kg) | 6 | 7/9 |
| | 3 | 1/9 |

Figure 3:
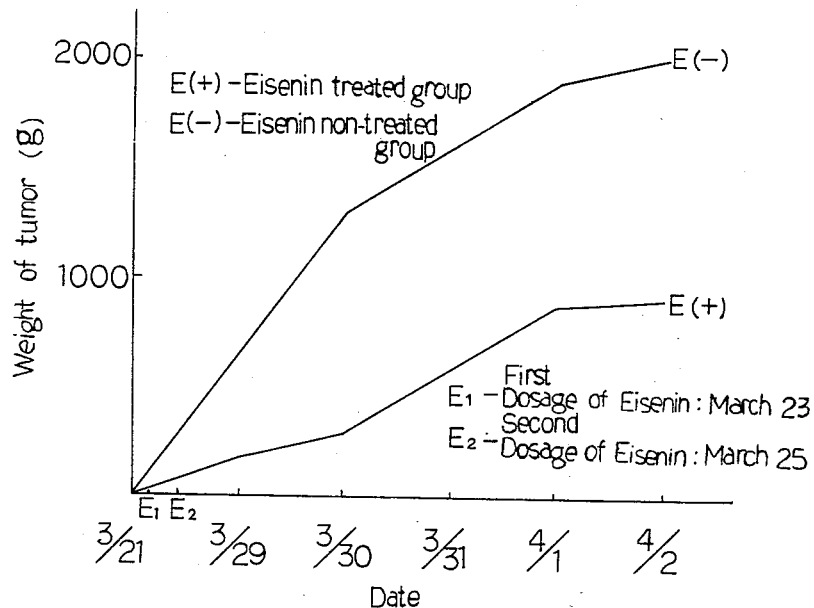
FIG. 3 is a graph showing the anti-tumor effect where the T-cells do not participate.
Figure 4:
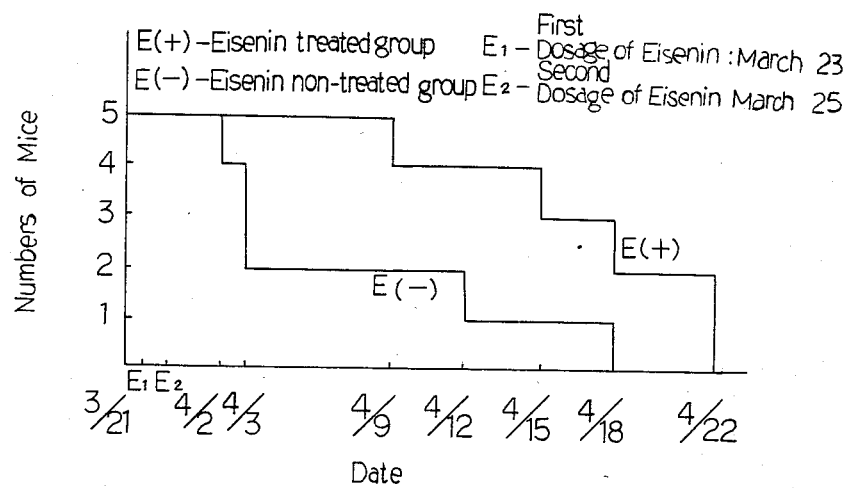
FIG. 4 is a graph showing the life prolonging effect of the same.
Figure 5:
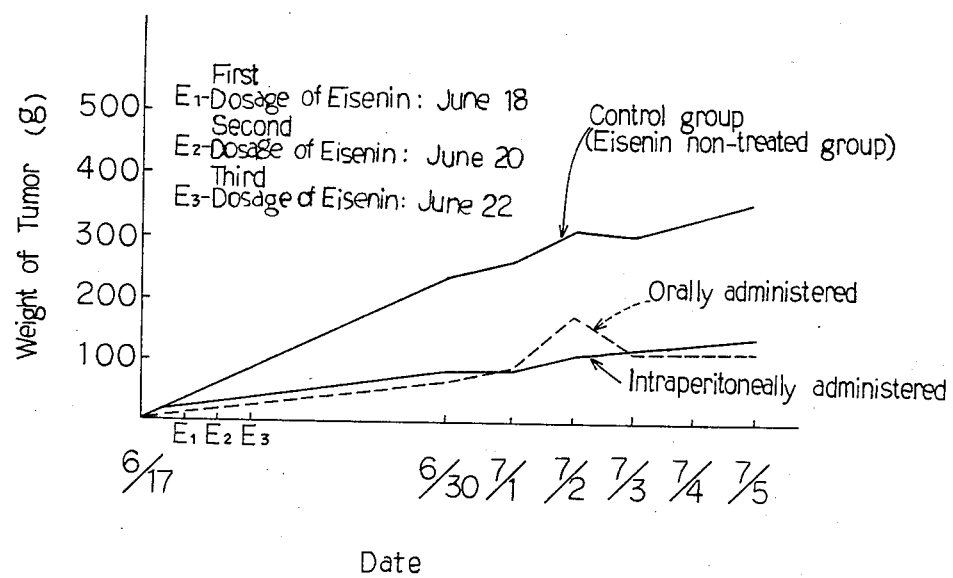
FIG. 5 is a graph showing the anti-tumor effect of Eisenin against the isologous xenogenic tumor.

To summarize the results of the assays described above, as demonstrated in the results in Table 1 and Table 2, in the case of such isologous allogenic tumor as Colon 26 against Balb/C mice, there is observed a significant difference between the Eisenin treated group and the Eisenin non-treated group, thus an anti-tumor effect of Eisenin is recognized; further as shown in FIGS. 3 and 4, also in the case of the nude mice free from T cells, similar results have been obtained; still further as shown in FIG. 5, also in the case of such isologous xenogenic tumor as Sarcoma 180 against Balb/C mice, a similar anti-tumor effect is recognized. On the contrary, as can be seen from the results of the delayed hyper-sensitivity test on Balb/C mice shown in Table 1, there is hardly any difference between the the average values of the four groups of combinations of the presence and absence of tumor transplantation and the presence and absence of treatment with Eisenin, and therefore Eisenin has no effect to activate the immunological action in which T cells participate, and also from the sensitivity test results shown in Table 2, the inhibition index (I.I.) is low in any case, which indicates no inhibition effect by Eisenin, that is, it may be recognized that there is no direct effect of Eisenin on tumor cells. In addition, in the results of the cytotoxicity test shown in Table 3, although there is no significant difference in the case of the spleen cells, there is a significant difference in the case of the intraperitoneal cells, and as the result, it can be recognized that the immunity imparting effect by Eisenin is mainly due to the activation of the adherent cells and the non-adherent cells in the peritoneal cavity. Furthermore, according to the acute toxicity test, the $LD_{50}$ of Eisenin is in the vicinity of 5 g/kg, and the effective dosage as estimated from the above various test results is suitably about 15 mg per 20 g based on the average body weight of Balb/C mice used in the experiments taken as 20 g, that is, about 75 mg/kg, and it is believed appropriate to administer this dosage in several doses.

We claim:

1. An immunopotentiating carcinostatic composition in pharmaceutical form, comprising Eisenin (tripeptide) of the general formula:

L-Pyrolgu-L-Gln-L-Ala wherein Pyroglu, Gln and Ala represent pyroglutamic acid, glutamine and alanine, respectively, and a pharmaceutically acceptable carrier or excipient to form an injectable solution, a tablet, an ointment, or a suppository.

2. The immunopotentiating carcinostatic composition as set forth in claim 1, wherein said pharmaceutical form is an injectable solution.

3. The immunopotentiating carcinostatic composition as set forth in claim 1, wherein said pharmaceutical form is a tablet.

4. The immunopotentiating carcinostatic composition as set forth in claim 1, wherein said pharmaceutical form is an ointment.

5. The immunopotentiating carcinostatic composition as set forth in claim 1, wherein said pharmaceutical form is a suppository.

6. The immunopotentiating carcinostatic composition according to claim 2, 3, 4 or 5 wherein the Eisenin is that obtained from *Eisenia bicyclis*.

7. The immunopotentiating carcinostatic composition according to claim 2, 3, 4 or 5 wherein the Eisenin is that obtained by synthesis.

* * * * *

UNITED STATES PATENT AND TRADEMARK OFFICE
CERTIFICATE OF CORRECTION

PATENT NO. : 4,543,350

DATED : September 24, 1985

INVENTOR(S) : Tatsuhei Kondo, Noboru Takabe, and Takeshi Horiba

It is certified that error appears in the above-identified patent and that said Letters Patent is hereby corrected as shown below:

On the title page, the Abstract should read:
ABSTRACT OF THE DISCLOSURE

A carcinostatic agent having an immunopotentiating carcinostatic effect which contains as an active ingredient Eisenin (tripeptide) of the general formula:

L-Pyroglu-L-Gln-L-Ala wherein Pyroglu, Gln and Ala represent pyroglutamic acid, glutamine and alanine respectively.

Signed and Sealed this

Twenty-fifth Day of February 1986

[SEAL]

Attest:

DONALD J. QUIGG

Attesting Officer

Commissioner of Patents and Trademarks